(12) United States Patent
Dubach

(10) Patent No.: US 11,253,665 B2
(45) Date of Patent: Feb. 22, 2022

(54) LARYNX MASK HAVING A CONNECTOR

(71) Applicant: Singularity AG, Maur (CH)

(72) Inventor: Werner F. Dubach, Maur (CH)

(73) Assignee: SINGULARITY AG, Maur (CH)

( * ) Notice: Subject to any disclaimer, the term of this patent is extended or adjusted under 35 U.S.C. 154(b) by 202 days.

(21) Appl. No.: 16/678,224

(22) Filed: Nov. 8, 2019

(65) Prior Publication Data

US 2020/0206444 A1   Jul. 2, 2020

Related U.S. Application Data

(60) Continuation of application No. 14/749,517, filed on Jun. 24, 2015, now abandoned, which is a division of
(Continued)

(30) Foreign Application Priority Data

Nov. 27, 2008 (CH) .................................. 1860/2008

(51) Int. Cl.
| | | |
|---|---|---|
| *A61M 16/04* | (2006.01) | |
| *A61M 16/08* | (2006.01) | |
| *B29C 65/48* | (2006.01) | |
| B29L 31/00 | (2006.01) | |

(52) U.S. Cl.
CPC ........ *A61M 16/0447* (2014.02); *A61M 16/04* (2013.01); *A61M 16/0409* (2014.02);
(Continued)

(58) Field of Classification Search
CPC .......... A61M 16/0486; A61M 16/0412; A61M 16/0409; A61M 16/0447; A61M 16/0816; A61M 2207/10; B29L 3031/753
See application file for complete search history.

(56) References Cited

U.S. PATENT DOCUMENTS 5,374,245 A   12/1994  Mahurkar
5,878,745 A *  3/1999  Brain ................ A61M 16/0456
                                                         128/207.15
(Continued)

FOREIGN PATENT DOCUMENTS

EP         1938855 A1    7/2008
WO      2006/125986     11/2006

OTHER PUBLICATIONS

International Search Report, Written Opinion and International Preliminary Report on Patentability for PCT/CH09/00370, filed Nov. 19, 2009.

*Primary Examiner* — Colin W Stuart
*Assistant Examiner* — Douglas Y Sul
(74) *Attorney, Agent, or Firm* — Paul D. Bianco; Stephen Bongini; Fleit Intellectual Property Law

(57) ABSTRACT

A larynx mask is provided that comprises a dorsal cover plate with an inflatable cuff integrally formed thereon and a tube connecting connector having an insertion section for connecting to an insertion tube. Two separate lumens are provided in the region of the insertion section, these being the esophageal lumen and a respiration lumen. These two lumens are separated from each other by a separating and supporting, wall. The separating and supporting wall extends from the insertion section to the tip of the larynx mask. While the esophageal lumen opens into an esophageal outlet at the proximal end of the mask, the respiration lumen opens in the ventral direction and is closed in the proximal direction close to the tip of the mask. Such a larynx mask is produced in one piece by way of injection of molding and is reinforced by the separating or supporting wall to prevent kinking.

16 Claims, 3 Drawing Sheets

Related U.S. Application Data application No. 13/130,467, filed as application No. PCT/CH2009/000370 on Nov. 19, 2009, now abandoned.

(52) U.S. Cl.
CPC .... *A61M 16/0415* (2014.02); *A61M 16/0427* (2014.02); *A61M 16/0816* (2013.01); *B29C 65/48* (2013.01); *A61M 16/0486* (2014.02); *A61M 2207/10* (2013.01); *B29L 2031/753* (2013.01)

(56) References Cited

U.S. PATENT DOCUMENTS

| | | | |
|---|---|---|---|
| 6,439,232 B1* | 8/2002 | Brain | A61M 16/0409 128/207.15 |
| 7,040,322 B2* | 5/2006 | Fortuna | A61M 16/0486 128/207.15 |
| 7,305,985 B2 | 12/2007 | Brain | |
| 7,506,648 B2 | 3/2009 | Brain | |
| 2001/0015207 A1* | 8/2001 | Pagan | A61M 16/04 128/207.15 |
| 2003/0037790 A1 | 2/2003 | Brain | |
| 2005/0039756 A1 | 2/2005 | Cook | |
| 2005/0229933 A1 | 10/2005 | McGrail | |
| 2006/0125986 A1 | 6/2006 | Choo | |
| 2006/0180156 A1* | 8/2006 | Baska | A61M 16/0409 128/207.15 |
| 2006/0201516 A1* | 9/2006 | Petersen | A61M 16/0409 128/207.14 |
| 2008/0099026 A1* | 5/2008 | Chang | A61M 16/0409 128/207.15 |
| 2010/0059061 A1* | 3/2010 | Brain | A61M 16/0409 128/207.14 |
| 2010/0126512 A1 | 5/2010 | Nasir | |
| 2011/0023890 A1 | 2/2011 | Baska | |

* cited by examiner

LARYNX MASK HAVING A CONNECTOR

REFERENCE TO RELATED APPLICATIONS

This application is a continuation of U.S. Ser. No. 14/749,517 filed Jun. 24, 2015, which is a divisional of U.S. Ser. No. 13/130,467, filed May 20, 2011, which is the US national phase entry of International Patent Application no. PCT/CH2009/000370, filed Nov. 19, 2009, which claims priority to Swiss patent application no. 1860/2008 filed Nov. 27, 2008. The disclosures of the related applications are incorporated herein by reference in their entireties.

FIELD OF THE INVENTION

The present invention relates to a larynx mask, comprising a dorsal cover plate with an inflatable cuff (5) circumferentially formed thereon and a tube connecting connector for connecting to at least one insertion tube which comprises an air supply lumen and an oesophageal lumen, and wherein the tube connecting connector has an insertion section.

BACKGROUND

Larynx masks of this type are known in many forms of embodiment and are inserted by means of a tube, known as a supraglottic tube, through the middle of the pharynx via the epiglottis of an anaesthetized patient. Larynx masks are usually supplied as a unit with the supraglottic tube formed on or attached thereto. This serves to keep open the airways and to ventilate a patient. At the same time such larynx masks also allow the introduction of tubes, probes, optical instruments and other instruments into the respiratory tract. More and more frequently such larynx masks have an oesophageal access. This allows the introduction of tubes into the oesophagus and the stomach in order to remove gastric juice and other fluids as well as air from the stomach. In anaesthetized patients emptying of the stomach is intended to prevent the stomach contents flowing back into the upper respiratory tract and being aspirated into the unprotected airways (windpipe, bronchi and lungs). A further advantage of an oesophageal access is the removal of passively or actively regurgitated stomach contents from the upper oesophagus to outside, which thereby represents limited, and thus inadequate, aspiration protection.

A large number of different larynx masks are known on the market. A typical example is set out in U.S. Pat. No. 5,878,745. This shows a gastro-laryngeal mask in which the supraglottic tube is a pipe through which several tubes can be fed. These tubes have lumens which are used for ventilation and for an oesophageal access. As a tube the oesophageal access must be passed through the entire larynx mask, fastened and passed through an outlet passing through the cuff. This is extremely time-consuming and requires a great deal of work.

Inserting a larynx mask is not always easy. Larynx masks with a relatively rigid supraglottic tube can be introduced more easily; however the rigidity prevents adaptation of the position of the larynx mask to the anatomical conditions. Insertion into the pharyngeal cavity by means of a relatively rigid supraglottic tube can result in injury, and positioning in the pharyngeal cavity is not always reliable.

Highly flexible larynx masks with corresponding highly flexible supraglottic tubes allow better positioning in the larynx but are more difficult and therefore occasionally more traumatic to insert and more difficult to position in the pharynx. More particularly, it often happens that when inserting such highly flexible larynx masks the proximal end of the larynx mask, known as the tip, is bent over. This means that reliable sealing of the larynx mask is no longer present. To remedy this problem a more rigid material can be resorted to, whereby, however, the advantages of the highly flexible materials are lost. The result is traumatic effects in the central pharyngeal cavity. Even with a slightly increased air pressure in the cuff this problem cannot always reliably be solved. In the larynx masks known today, the oesophageal outlet always passes through the cuff. This complicates the entire manufacturing of the larynx mask. If kinking or even just slightly greater bending of the tip of the larynx mask occurs, the oesophageal outlet is mostly then no longer free and an instrument or a tube can no longer be passed through.

A larynx mask is known from U.S. Pat. No. 5,878,745 in which the larynx mask itself is made more rigid by passing through an oesophageal access in the longitudinal direction. This oesophageal access is placed in the center. Although this increases the longitudinal rigidity of the larynx mask, it unfavorably affects its height. Also, the patient's pharynx must be protected by means of an additional inflatable dorsal cuff.

From WO 2006/125986 and US 2003/0037790 different versions of larynx masks are known in which the oesophageal access is formed either by a separately insertable tube or by an integrally formed lumen. In both cases, however, the course of the oesophageal opening in the mid longitudinal axis has the aforementioned disadvantages.

A presumably not manufacturable larynx mask is shown by a solution in which the insertion tube runs from outside the patient continuously to the tip of the oesophageal outlet and two integral cuffs are present on the one hand to delimit the respiration chamber and on the other hand to seal the oesophageal outlet.

SUMMARY

It is therefore the dual aim of the present invention, in addition to avoiding the described drawbacks of the prior art, to improve a larynx mask in such a way that it is easier to produce and, more particularly, so that difficult insertion of a tube for forming the oesophageal passage can be avoided, and that even with the use of a highly flexible material said problems no longer occur, or their occurrence is greatly reduced.

This aim is achieved by a larynx mask comprising a dorsal cover plate with a circumferential inflatable cuff formed thereon and a tube connecting connector for connecting to at least one insertion tube, wherein the larynx mask comprises an air supply lumen and an oesophageal lumen and the tube connecting connector has an insertion section. The tube connecting connector, after the insertion section, has a separating or supporting wall running in the longitudinal direction of the larynx mask from its distal to at least approximately its proximal end and separating a closed lumen as the oesophageal lumen and an open lumen as a respiration lumen, which opens into a respiration space under the cover plate which can be sealed by the cuff.

Overall the longitudinal division, in accordance with the invention, of the area of the larynx mask below the cover plate by the separating and supporting wall brings about a strengthening of the larynx mask against kinking, whereby the first part of the task is achieved, while at the same time, as the separating wall is part of a continuous closed lumen, serving as the oesophageal lumen, the entire manufacture of the larynx mask is considerably simplified with regard to its assembly. Thus it is no longer necessary for a separate tube to be pulled through the larynx mask and attached therein as the oesophageal lumen is formed in one piece with the larynx mask. Due to the straight course and conical narrowing of the oesophageal opening from the tube connecting connector with the largest diameter to the outlet opening defining the smallest diameter, such an opening can be manufactured in one piece by means of a simple slide.

BRIEF DESCRIPTION OF THE DRAWINGS

In the drawings a preferred example of an embodiment of the subject matter of the invention is shown and is explained with the aid of the following description.

DETAILED DESCRIPTION

Figure 1:
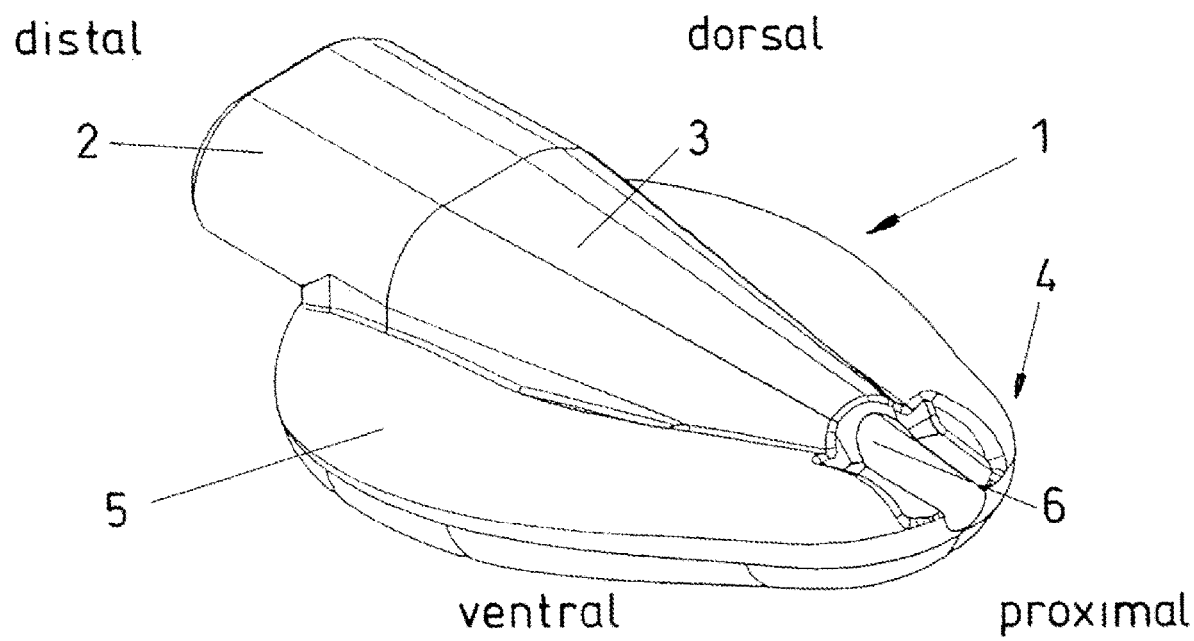
FIG. 1 shows a perspective overall view of a larynx mask in accordance with the invention looking at the dorsal cover plate.

FIG. 1 shows the larynx mask which is denoted overall with 1. An insertion tube is attached to this larynx mask but is not shown in the drawing. However, for this a tube connecting connector 2 is used. This tube connecting connector 2 transits into a cover plate 3 and cuff 5 also formed thereon in one piece. The entire larynx mask 1 from the tube connecting connector 2 on the distal end to the tip 4 on the proximal end of the larynx mask is produced in one piece and accordingly all of the same synthetic material. In FIG. 1 the circumferential cuff 5 can be seen which is reduced in diameter by an oesophageal outlet 6 only on the proximal end at the tip 4 whereas at the distal end the cuff 5 passes through under the tube connecting connector 2. At the proximal end the oesophageal outlet 6 passes over the cuff 5 in a type of channel.

Figure 2:
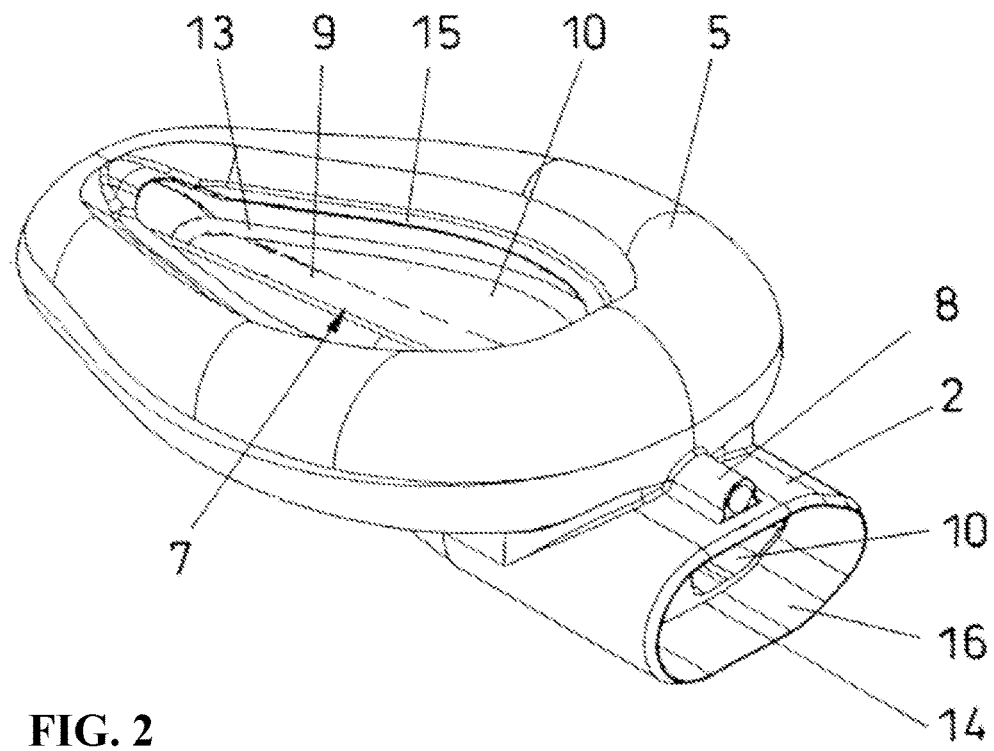
FIG. 2 again shows a perspective overall view of the same larynx mask, but looking at the ventrally arranged cuff.
Figure 3:
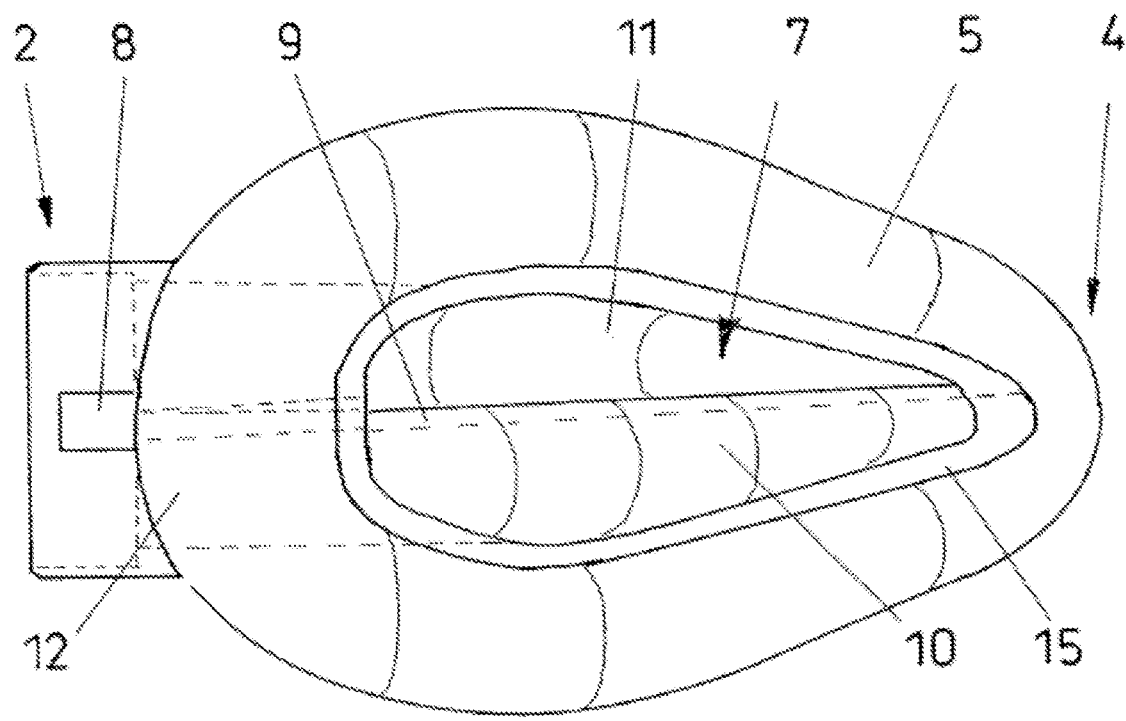
FIG. 3 shows a vertical view of the larynx mask on the ventral side.
Figure 4:
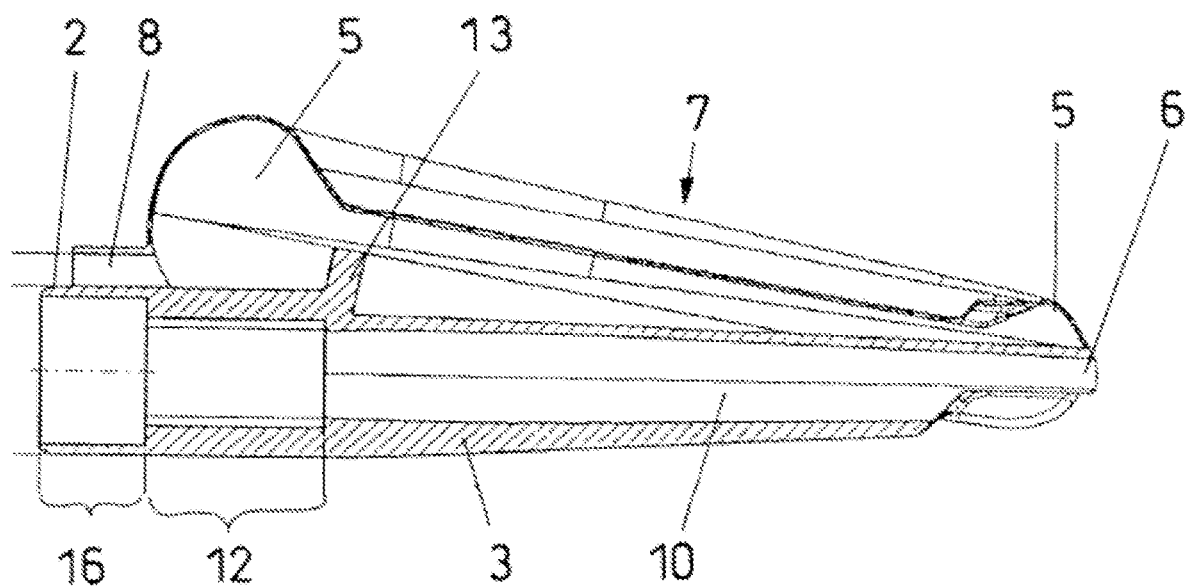
FIG. 4 shows a longitudinal section through the larynx mask in the direction of the course of the oesophageal lumen.

The cuff 5 is produced by open injection molding. In particular, in the cross-sections shown in FIGS. 6 and 7, but also in FIG. 2, a circumferential thickened adhesive, welding wall 13, practically following the peripheral edge of the cover 3, can be seen, while at the same time the lower edge of the cuff 5, here still shown as open, is also provided with a circumferential adhesive, welding edge 15. Only through adhering or welding the adhesive, welding edge 15 to the corresponding circumferential adhesive, welding wall 13 is the closed circumferential cuff 5 produced. This cuff 5 is inflated and deflated via a ventilation connection 8 which is on the ventral side of the tube connecting connector 2. This ventilation connection 8 can be clearly seen in FIGS. 2-4.

The circumferential adhesive or welding wall 13 delimits a respiration chamber 7 below the cover plate 3.

As has already been stated an insertion tube, which is not shown here, is introduced into the tube connecting connector 2. This insertion tube advantageously, but not necessarily, consists of a single plastic tube with two lumens which in terms of shape and size are matched to the lumens present in the larynx mask. To make this connection of the larynx mask to the insertion tube as simple as possible, the tube connecting connector 2 has a plug section 16 which can be seen in particular in FIGS. 2 and 4. The plug section 16 is not divided into two lumens, as preferably an insertion tube is inserted here which has two lumens in the same form as in the insertion section 12 following on from the plug section 16. This insertion section 12 runs at least approximately under the area in which the two lumens 10 and 11 extend over the cuff 5. Although in FIG. 4 it appears as if these areas pass under the cuff 5, this is only due to illustration in which the ventral side is shown facing upwards instead of the dorsal side.

Following the plug section 16 of the tube connecting connector 2 there is, as has been stated, an insertion section 12. In this area two separate lumens can be seen which are both closed in this area, namely the oesophageal lumen 10 and the respiration lumen 11. This is most clearly seen in FIG. 5. Running between these two lumens 10 and 11 at least approximately perpendicularly to the cover 3 is a separating and supporting wall 9. Through this separating and supporting wall which passes through the larynx mask in around the middle, the larynx mask is provided overall with increased rigidity which counteracts any kinking.

In an advantageous embodiment the separating and supporting wall 9 can have a sack-like intermediate chamber which is closed until near to the tip and which can accommodate a reinforcing element.

Figure 5:
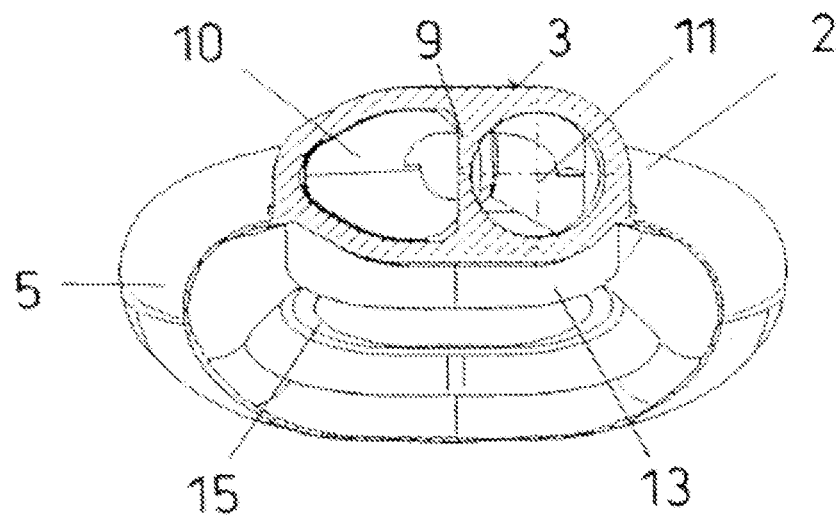
FIG. 5 shows a cross-section through the larynx mask in the area of an insertion section looking towards the proximal end and the oesophageal outlet 6.

The thickened adhesive, welding wall 13, which is not in cross-section in FIG. 5, increases the rigidity of the larynx mask. It can be clearly seen that the cuff is not yet closed by welding or adhesion and accordingly the adhesive and/or welding edges 15 can be seen. After the end of the insertion section 12, the oesophageal lumen 10 continues to be closed, while the respiration lumen 11 opens into a practically U-shaped channel as can be clearly seen in FIGS. 6 and 7. Both figures show the same cross-section at the same point, but in FIG. 6 the view is directed towards the proximal end. The separating and supporting wall 9 remains unchanged through the absence of the ventral wall section of the respiration lumen 11. In these figures it can also be seen that the diameter of the two lumens, namely the oesophageal lumen 10 and the respiration lumen 11, and therefore also the separating and supporting wall 9 runs downwards from the cover plate 3 in the ventral direction less far than the circumferential adhesive or welding wall 13. The end of this adhesive or welding wall 13 spans a plane and this plane is neither pierced by the two lumens 10 and 11 nor by the wall 9.

Figure 6:
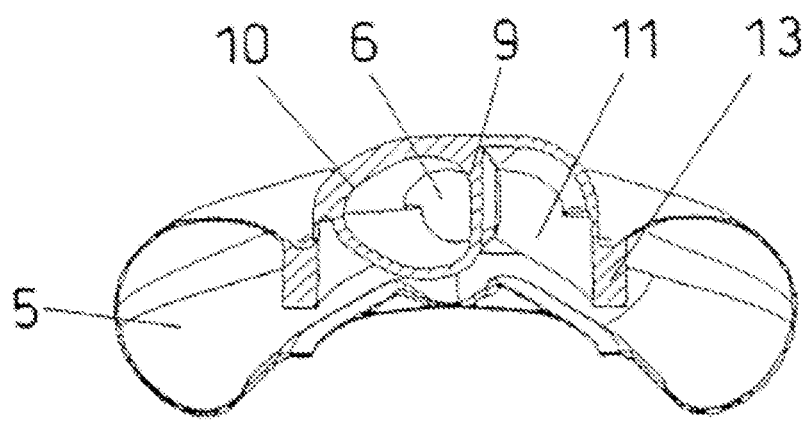
FIG. 6 again shows a cross-section through the same larynx mask in the central area of the longitudinal extent of the larynx mask whereby the direction of viewing is again towards the proximal end.
Figure 7:
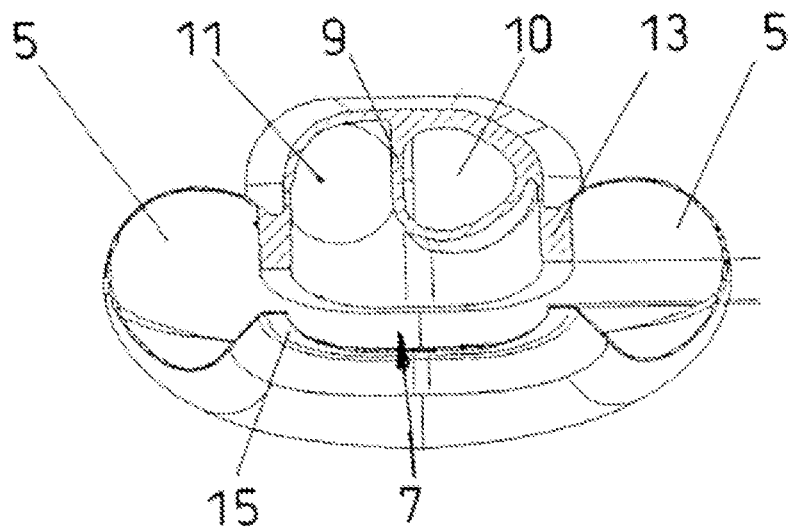
FIG. 7 shows the same cross-section at the same point, but looking towards the distal end of the larynx mask.

In this way a relatively large respiration chamber 7 remains under the two lumens 10 and 11 and the separating and supporting wall 9. It can be seen that after the insertion section 12 from where the respiration lumen 11 opens out this space directly merges with the respiration chamber 7. In FIG. 6 which shows the diametric section through the larynx mask looking towards the proximal end, it can be seen that the oesophageal lumen 10 is open towards the oesophageal outlet 6, while the respiration lumen 11 is limited in the proximal direction by the adhesive or welding wall 13.

As has already been stated the insertion tube is not shown here. Preferably, in cross-section such an insertion tube will be shaped like the tube connecting connector 2 in the cross-section area in accordance with FIG. 5. However, this is not obligatory. For example, an adapter, into which two individual tubes open which together form an insertion tube 2, can be inserted into the plug area 16 up to the projection 14.

LIST OF REFERENCE NUMBERS

1. Larynx mask
2. Tune connecting connector
3. Cover plate
4. Tip of the larynx mask
5. Cuff
6. Oesophageal outlet
7. Respiration chamber
8. Cuff ventilation connection
9. Separating and supporting wall
10. Oesophageal lumen
11. Respiration lumen
12. Insertion section
13. Adhesive, welding wall
14. Projection
15. Adhesive, welding edge
16. Plug area

The invention claimed is:

1. A larynx mask formed as a single piece comprising:
    (i) a dorsal cover plate with a circumferential inflatable cuff formed thereon;
    (ii) a tube connecting connector having an insertion section for connecting to at least one insertion tube;
    (iii) a respiration lumen and an oesophageal lumen;
    (iv) a separating and supporting wall formed substantially centrally on the cover plate, wherein the separating and supporting wall extends longitudinally in a ventral direction from the cover plate;
    (v) a circumferential adhesive or welding wall positioned on the cover plate, the circumferential adhesive or welding wall extending longitudinally in a ventral direction from the cover plate towards a lower edge of the cuff, and being thickened relative to a wall of the cuff; and
    (vi) a circumferential adhesive or welding edge formed on the lower edge of the cuff and extending in a dorsal direction towards the circumferential adhesive or welding wall,
    wherein in an area of the insertion section of the tube connecting connector, the separating and supporting wall forms a bi-luminal tube separating the respiration lumen from the oesophageal lumen, and
    the separating and supporting wall extends downwardly from the dorsal cover plate in a ventral direction less far from the cover plate than the circumferential adhesive or welding wall.

2. The larynx mask of claim 1 formed by injection molding.

3. The larynx mask of claim 1, wherein the separating and supporting wall extends perpendicular to the dorsal cover plate.

4. The larynx mask of claim 1, wherein the separating and supporting wall extends to an oesophageal outlet, which is formed by an opening in the dorsal cover plate and extends over the inflatable cuff.

5. The larynx mask of claim 1, wherein a cross-section of the respiration lumen is larger than a cross-section of the oesophageal lumen in an area of the insertion section.

6. The larynx mask of claim 1, wherein the insertion section is limited by a projection that narrows a cross-section of the insertion section and serves as a stop for the at least one insertion tube.

7. The larynx mask of claim 1, wherein the separating and supporting wall and the circumferential adhesive or welding wall extend parallel to one another.

8. The larynx mask of claim 1, wherein the circumferential adhesive or welding wall delimits a respiration chamber below the dorsal cover plate.

9. A larynx mask formed as a single piece comprising:
    (i) a dorsal cover plate with a circumferential inflatable cuff formed thereon;
    (ii) a tube connecting connector having an insertion section for connecting to at least one insertion tube;
    (iii) a respiration lumen and an oesophageal lumen each in functional contact with the at least one insertion tube;
    (iv) a separating and supporting wall formed substantially centrally on the cover plate, wherein the separating and supporting wall extends longitudinally in a ventral direction from the cover plate and extends from the tube connecting connector to an oesophageal outlet, above the cuff;
    (v) a circumferential adhesive or welding wall positioned on the cover plate, the circumferential adhesive or welding wall extending longitudinally in a ventral direction from the cover plate towards a lower edge of the cuff, and being thickened relative to a wall of the cuff; and
    (vi) a circumferential adhesive or welding edge formed on the lower edge of the cuff and extending in a dorsal direction towards the circumferential adhesive or welding wall, and
    wherein the dorsal cover plate, the tube connecting connector, the respiration lumen, the oesophageal lumen, and the separating and supporting wall are all made from the same material, and
    the separating and supporting wall extends downwardly from the dorsal cover plate in a ventral direction less far from the cover plate than the circumferential adhesive or welding wall.

10. The larynx mask of claim 9 formed by injection molding.

11. The larynx mask of claim 9, wherein the separating and supporting wall extends perpendicular to the dorsal cover plate.

12. The larynx mask of claim 9, wherein the oesophageal outlet is formed by an opening in the dorsal cover plate and extends over the inflatable cuff.

13. The larynx mask of claim 9, wherein a cross-section of the respiration lumen is larger than a cross-section of the oesophageal lumen in an area of the insertion section.

14. The larynx mask of claim 9, wherein the insertion section is limited by a projection that narrows a cross-section of the insertion section and serves as a stop for the at least one insertion tube.

15. The larynx mask of claim 9, wherein the separating and supporting wall and the circumferential adhesive or welding wall extend parallel to one another.

16. The larynx mask of claim 9, wherein the circumferential adhesive or welding wall delimits a respiration chamber below the dorsal cover plate.

\* \* \* \* \*